(12) United States Patent
Campbell et al.

(10) Patent No.: US 12,239,375 B2
(45) Date of Patent: Mar. 4, 2025

(54) METHODS AND APPARATUS FOR IMPROVING IMAGES DURING VISUALIZATION OF THE RETINA

(71) Applicants: Melanie C W Campbell, Waterloo (CA); Julia Zangoulos, Kitchener (CA)

(72) Inventors: Melanie C W Campbell, Waterloo (CA); Julia Zangoulos, Kitchener (CA)

( * ) Notice: Subject to any disclaimer, the term of this patent is extended or adjusted under 35 U.S.C. 154(b) by 479 days.

(21) Appl. No.: 17/722,772

(22) Filed: Apr. 18, 2022

(65) Prior Publication Data
US 2022/0330816 A1 Oct. 20, 2022

Related U.S. Application Data

(60) Provisional application No. 63/175,915, filed on Apr. 16, 2021.

(51) Int. Cl.
| | |
|---|---|
| *A61B 3/10* | (2006.01) |
| *A61B 3/00* | (2006.01) |
| *A61B 3/12* | (2006.01) |
| *A61B 3/14* | (2006.01) |
| *G01J 9/00* | (2006.01) |

(52) U.S. Cl.
CPC .......... *A61B 3/1015* (2013.01); *A61B 3/0025* (2013.01); *A61B 3/12* (2013.01); *A61B 3/14* (2013.01); *G01J 9/00* (2013.01)

(58) Field of Classification Search
CPC ....... A61B 3/1015; A61B 3/0025; A61B 3/12; A61B 3/14; G01J 9/00
See application file for complete search history.

(56) References Cited

U.S. PATENT DOCUMENTS

2020/0237214 A1* 7/2020 Glik .................... A61B 3/14

OTHER PUBLICATIONS

J J Hunter, C J Cookson, ML Kisilak, JM Bueno, and M C W Campbell (2007), "Characterizing image quality in a scanning laser ophthalmoscope with differing pinholes and induced scattered light", Journal of the Optical Society of America A, vol. 24, Issue 5, 1284-1295.
Donnelly WJ, Roorda, A, (2003). Optimal pupil size in the human eye for axial resolution, J. Opt. Soc. Am. A 20, 2010-2015.
(Continued)

*Primary Examiner* — James C. Jones
(74) *Attorney, Agent, or Firm* — HILL & SCHUMACHER

(57) ABSTRACT

Methods and apparatus for producing images of the retina or fundus with improved quality and visualization of its features. This is accomplished by adjustment of specific pupil size, pupil position, detector pinhole size and wavelength parameters of the instrument to give improved image quality as described by a chosen image quality metric. Methods are less complex than adaptive optics and give an improved image in a region of interest and potentially over a larger field of view. Thus, it will be useful in instruments designed for the screening of retinal disease(s). The methodology is applicable to an individual's eye, on the basis of either the group that said individual falls into or measurements of the quality of their eye's optics. As described herein, the settings (including optimum pupil size, pupil position, detector pinhole size and/or wavelength for imaging) can be chosen to give improved the retinal image quality.

20 Claims, 5 Drawing Sheets

(56) References Cited

OTHER PUBLICATIONS

LaRocca, F; Dhalla, A, Kelly, M, Farsiu, S and Izatt, J, (2013), "Optimization of confocal scanning laser ophthalmoscope design", J Biomed Opt. 18(7): 076015. Incorrectly given in the text as Izatt (2013), 10 pages.

Navarro, R, (2014), "Adaptive model of the aging emmetropic eye and its changes with accommodation", Journal of Vision November vol. 14, 21. doi:https://doi.org/10.1167/14.13.21, 1-17.

Wilson, M.A., Campbell, M.C.W. and Simonet, P., (1992), "The Julius F. Neumueller Award in Optics, 1989: Change of pupil centration with change of illumination and pupil size", Optometry and Vision Science 69, 129-136.

Simonet, P. and Campbell, M. C. W., (1990), "The optical transverse chromatic aberration on the fovea of the human eye", Vision Research, vol. 30, Issue 2, 187-206, https://doi.org/10.1016/0042-6989(90)90035-J.

Thibos, L. N., Bradley, A., Still, D. L., Zhang, X., Howarth, P.A., (1990), "Theory and measurement of ocular chromatic aberration", Vision Research, vol. 30, Issue 1, 33-49. https://doi.org/10.1016/0042-6989(90)90126-6.

\* cited by examiner

| AGE | 20-32 | | 58-70 | |
|---|---|---|---|---|
| | OPS (mm) | LR (μm) | OPS (mm) | LR (μm) |
| Average | 3.09 | 3.95 | 2.73 | 4.48 |
| SD | 0.488 | 0.654 | 0.402 | 0.654 |

METHODS AND APPARATUS FOR IMPROVING IMAGES DURING VISUALIZATION OF THE RETINA

CROSS-REFERENCE TO RELATED APPLICATION

This patent application relates to, and claims the priority benefit from, U.S. Provisional Patent Application No. 63/175,915: Methods and Apparatus for improving Images during Visualization of the Retina; Filing date 16 Apr. 2021, the whole content of which is incorporated herein by reference in its entirety.

FIELD

The subject matter of this application relates to method and apparatus to improve the imaging the retina of the eye (retinal or fundus imaging instrument) so as to give images of the retina or fundus which have improved quality, which can be quantified by many metrics including resolution, contrast or other metrics discussed below.

BACKGROUND

Others have previously addressed the design of instruments used to image the retina (including the fundus) when considering the imperfections in the optics of the eye using two approaches. The first design which we have modified and extended, was by Donnelly and Roorda, 2003 used measurements of the optical quality of the eyes of fifteen young individuals to calculate the depth resolution possible when imaging the eye. They also determined the different optimal pupil sizes which gave the best depth resolution (axial) and lateral resolution for the same group. The study was limited to a small number of younger individuals so it is unclear whether the pupil sizes given applied more broadly to young individuals and older individuals. Since the optical quality of the eye may change with age due to both scattered light and aberrations (Artal, 1993) the specified pupil sizes are unlikely to apply to other ages. Axial resolutions were best with larger pupils, averaging 4.30±1.19 mm. Lateral resolutions are best with smaller pupils, averaging 2.46±0.66 mm. Determining the optimum pupil size for improving the quality of retinal images as a function of wavelength and/or the group (as an example defined by age) that an individual falls into has not been previously described. A single, very small detector (confocal) pinhole was used. A small detector pinhole is preferable if depth resolution is the most important consideration. But by trimming the wide angle scattered light component of the point spread function, a pinhole at the detector is also known to increase the contrast of images of the retina and fundus.

The paper by Izatt and coauthors, (LaRocca, 2013) discussed the choice of pinhole size in the detection arm (detector pinhole size) in an imaging instrument when a metric measuring the quality in a single imaging plane is the most important consideration. The ideal detector pinhole size was found experimentally for a single normal human individual (whose age was not given) by determining the effect of the confocal pinhole on throughput and sharpness of the resultant images of cone photoreceptors in the retina at a small eccentricity from the fixation point (approximately 4 deg). Again, the study of only one participant, considering only their optical quality at a particular location on the retina limits the generalizability of the result. Their instrument design used "a pupil configuration similar to the original SLO except that we illuminate through a larger portion of the pupil and collect over the entire pupil." This makes sense for younger participants. However, in older participants, the natural pupil may not allow this configuration and larger aberrations may reduce image quality. Furthermore, they based their optimal pupil sizes on the 15 young individuals described by Donnelly and Roorda (2003) with the limitations described above. Thus, it is unclear that the measurements can be generalized. Their methods differed in significant ways from those used in this application.

One of us co-authored a paper (Hunter et al, 2007) where we quantified image quality by direct measurement of retinal images, applying metrics (signal to noise ratio, entropy and acutance) to directly measure the quality of retinal images using calculations applied to the image themselves. These metrics were then studied as a function of artificially induced scattered light, detector pinhole size and defocus. Unlike in the methods described herein, for the imaging, a single pupil size was used across all ages. One detector pinhole size was identified as best when considering all ages. For one of the metrics and one detector pinhole size, image quality, linearly decreased with age. It was concluded that entropy was a good metric with which to monitor the quality of retinal images.

Another group showed that the images of some retinal structures which scatter light can be improved by offsetting the detector pinhole from the source (Elsner, 2000) so that it accepts the scattered light. Methods have been published to measure the amount of light scattered in an individual eye in the presence of cataract (Schram, 2021). And there are several objective scales for the severity of cataract and the amount of light scattered (Cochener, 2015). In addition, wavefront errors have been shown to increase in eyes with cataracts compared to those in eyes without cataracts (Kuroda, 2002).

The work herein varies wavelength, pupil size, pupil centration and on axis pinhole detector size to give optimal settings for an individual or a group of individuals who share a particular characteristic. Methods are described to further improve retinal image quality in a more individualized way, taking account of age, any ocular condition potentially affecting image quality (including the amount of scattered light and ocular aberrations). Besides cataract discussed above other conditions are known to increase aberrations and scattered light within the eye and by extension impact the quality of a retinal image, including but not limited to age (Artal, 1993) and diabetes (Shahidi, 2004, Adnan, 2015), where the amount of light scattered from the cornea increased (Özyol, 2018) with diabetes duration as did the Hartmann-Shack spot size which did not decrease after wavefront correction (Valeshabad, 2014), likely due to an increase in scattered light compared to those without diabetes. Another study (Liu, 2019) showed that all measures of image quality in eyes with diabetes, whether related to optical wavefront errors or to scattered light, worsened compared to age matched normal participants. Our own study (unpublished) FIG. 4 confirms that optical quality is worse in those with diabetes and shows for the first time that the optical quality worsens as a function of the duration of the disease. The same study showed that these markers in normal participants also worsened as a function of age.

Although image quality decreases due to both increasing aberrations and increased light scatter, van den Berg (2017) suggested that aberrations blur the central part of the point spread function (PSF) while scattered light (straylight) influences the outer part of the PSF. Consistent with this, an objective scatter index has been defined which is the ratio of the amount of light within an annular area of 12 and 20 min of arc (inner and outer radii) and that recorded within one minute of arc of the central peak in the acquired double-pass image when the person is looking at a point source. The OSI is elevated in the presence of cataract (Sahin, 2016) and diabetes (Liu, 2019).

Many eye models give image quality of the eye as a function of eccentricity on the retina and these include models for younger adults (Goncharov and Dainty, 2007) and eye models as a function of age for example Navarro, 2014. The predictions in these models of optical quality often agree with experimental measurements. They take account of natural pupil decentration and allow the calculation of image quality as a function of pupil size. In previous work, this calculation is made for the natural pupil centration. But Campbell and co-authors have shown that the pupil centre moves as the intensity of illumination drives changes in pupil size (Wilson, 1992) and that a change in the position of the pupil centre changes the aberrations of the eye (Bing, 1994). The comparison of eye models versus human data normally includes values of subtotals of types of aberrations but does not compare the aberrations structure across the pupil with that of individual eyes. Thus, the effects of pupil decentration are not explicitly considered.

Customized eye models for individuals are also available, which reproduce the magnitude of aberrations of that individual (Navarro, 2006), again for a natural pupil size and centration. Potential image quality improvements for an adjustable artificial pupil superimposed on the natural pupil were not considered. Unlike previous work, we consider the changes in both pupil size, pupil centration and detector pinhole size needed for image quality improvements.

One method used in retinal (fundus) imaging systems to improve the quality of retinal images is adaptive optics correction of optical imperfections of the eye. It is also used in microscopes and astronomical images. When used when imaging the retina of the eye, this method usually combines the sensing of wavefront errors and their correction (Liang, 1997). Some, including Campbell (Roorda, 2002) have corrected the optical imperfections of individual eyes (wavefront error correction) in real time allowing its use with a confocal scanning laser ophthalmoscope to produce video rate images. The wavefront correction is iterated until the image quality (determined by a metric) is optimised. Correction by adaptive optics is complex with expensive components and produces a small field of view in high resolution.

The above methodology corrects the optics most often for the central retina or over a small field of view and needs to iterate the correction as the position on the retina being imaged is changed. These systems are complex because of the cost of adaptive optics and control systems and because the measurements and corrections must be made rapidly. Thus, they are not suited for instruments designed either to be low cost, less complex, easy to use, having a wide field of view, potentially slower to acquire images or to screen the retina for systemic and retinal diseases in a variety of settings. settings. The methods described are even more complex to implement on instruments designed to image a larger field of view.

However, the optical imperfections of the eye do reduce the quality of images of the retina (and fundus). Methods to improve the quality of retinal images are important to the detection of retinal and systemic disease.

SUMMARY

Herein we describe the methods and apparatus to improve the image quality of the retina in an instrument(s) designed to image the retina and fundus of the eye with improved image quality for individuals in instruments with a wider field of view without the use of other more expensive methods like adaptive optics which result in high resolution but a small field of view. Compared to instruments using adaptive optics to correct the eye's optics, the described implementation will be lower cost and less complex, easier to use, have a wider field of view, will potentially be slower to acquire images and will be suited among other uses to screen the retina for systemic and retinal diseases, including for ocular diseases and/or biomarkers of systemic or brain diseases in a variety of settings.

We start with and analysis of the advantages of imaging in an infrared wavelength, including a novel analysis of the smaller decrease in resolution in moving from visible light to infrared light for the imaging in a system like the eye with higher order aberrations.

We wish to reduce the effects of the optical imperfections (aberrations and scattered light of the eye which reduce the quality of images of the retina (and fundus). The improvement in image quality of the resulting images may be confirmed using previously developed overall metrics applied to images or from the calculated image quality or inferred from the observed resolution or contrast of features on the retina. These improvements in turn will result in improved detection of changes in the retina expected early in retinal diseases and as biomarkers of systemic disease. Thus, they will likely result in improved diagnosis of disease.

In order to develop methods to improve lateral and or depth resolution in individuals we derive our methods from the study of a much larger number of individuals than previously used, both within and across age groups rather than the characteristics of a few younger normal individuals, considered by previous authors when discussing ideal pupil or detector pinhole sizes for image quality improvements in depth and lateral resolution. Unlike previous work, we also consider the changes in pupil size, pupil centration, detector pinhole size and wavelength which in combination will provide greater retinal image quality improvements, mitigating both the effects of optical aberrations and the effects of scattered light while simultaneously offering the advantage of longer wavelengths reducing the need for pupil dilation. In the implementations presented, we consider pupil centration, detector pinhole size and/or wavelength in combination with pupil size. When optimizing more than one variable, we consider them in a particular order. Furthermore, unlike previous work, we apply our methodology not just to young normal individuals but to normal individuals as a function of age and also to individuals who are known to have differences in the optics of their eyes due either due to ocular or systemic diseases. As an example, we use our methodology to show that the optimum pupil sizes required for individuals with diabetes differ from the pupil sizes of those without the disease and that the pupil sizes needed are a function of their disease duration. We teach how this approach could be extended to other conditions or other measures of disease status for example to eyes with cataracts which also have both increased ocular wavefront aberrations and scattered light, compared to the eyes of those without cataract.

When varying wavelength in an optical imaging system, the diffraction limited spot size and the resolution of the systems gets larger (poorer) proportional to the increase in the wavelength of light from the visible to the infrared for small pupils. But the eye suffers from aberrations in monochromatic light which have been shown in microns to remain almost constant with wavelength (Marcos, 1999; Fernandez, 2008, Bueno, 2010). For our dataset starting with higher order monochromatic aberrations in normal eyes at 550 nm, we modelled the monochromatic aberrations as constant with wavelength, as a function of pupil size (see pupil section for details). We calculated retinal point spread functions and associated image quality metrics as a function of pupil size at different wavelengths. For small diffraction limited pupil sizes, diffraction predicted a 50% increase in the radius of 50% encircled energy (a metric of resolution). However, above a 3.35 mm pupil diameter, the radius of 50% encircled energy and resolution remain constant for a given pupil size with increasing wavelength (FIG. 6). On average, the optimum pupil size (corresponding to the best resolution) increased with increasing wavelength. The corresponding best lateral resolution worsened only by 30% from 4.5 microns in green light to 5.9 microns in infrared light, much less than the 50% decrease in the diffraction limit. Moreover, when imaging with pupils larger than 3.45 mm, the image quality is independent of wavelength. This is a novel result which points to advantages of imaging with infrared light (FIG. 6). There may however be more light scattered from deeper in the retina in infrared light (Bueno, 2010).

Once the wavelength has been chosen, we vary pupil size and centration and detector pinhole size. And we consider the optimum pupil sizes and centration and pinhole sizes needed for several measures of image quality, in addition to measures of resolution, previously considered by others in specifying optimum pupil sizes for a few young individuals. We also include more global measures of image quality like the area under the modulation transfer function which is a measure of contrast across feature sizes. We show that the choice of optimal (optimum) pupil size and detector pinhole size is different for different for the different image quality metrics considered.

Modelling of the image quality on the retina as a function of instrument parameters is one step in describing the parameters for improvement of image quality. This can involve an extension of the methodology used previously which produces an eye model with 1) a phase plate which describes the measured wavefront errors for an individual eye and 2) a paraxial power which focuses the light onto the retina. From this the image quality on the retina at or near the optical axis, can be calculated as a function of pupil size as previously described. Here, as a demonstration, we extend the calculation to a large number of eyes (~1200) in various age groups, rather than the few at only young ages, previously analysed. From this we have shown that the optimum pupil size is age dependent. The method has been automated to repeat the calculation as a function of pupil size (and if desired the position of the instrument's pupil within the natural (or dilated) pupil of the eye (referred to as pupil centration). Then the optical quality for each variable is assessed and the optimal pupil size and centration is given by the combination that produces the best image quality for the metric chosen. The metrics calculated in the implementations described include, in addition to lateral and depth resolution, the Strehl ratio, the Hopkins ratio (Mouroulis, 2022) and the contrast in the modulation transfer function at a particular spatial frequency. The groups of individuals for which the optimums were calculated include a larger number of young adults than previously considered and many in other age groups up to 70 years old. In addition, any group whose ocular or systematic conditions change their ocular optics can be considered. An example is given of the method and implementation for a group of individuals with diabetes.

Alternately, an average eye model that well represents the eyes' optical quality for a particular group of individuals, for instance an eye model which allows the variation of modelled aberrations with age (Navarro, 2014) could be used to produce the images on the retina as a function of instrument pupil size. But because the models don't usually consider pupil decentration explicitly, they would not allow modelling of pupil centration, or the pinhole detector. Herein, we also describe how to determine the aberrations as a function of wavelength of illumination and how to determine the optimum detector pinhole.

This intellectual property discloses methods and apparatus for the imaging and visualization of the retina and its features that improves one or more of the visibility, contrast and resolution of retinal features through improvement of metrics of the quality of either the optical image formed on the retina or the quality of the image itself. As well as those mentioned above and considered in the literature cited below, metrics can include but are not limited to one or more of lateral resolution, depth resolution, Strehl ratio, Hopkin's ratio, overall image contrast, contrast of specific feature sizes and metrics which analyze the quality of the resulting retinal image. The methodology is disclosed in two main implementations, either of which can be applicable to a given individual or a group of individuals with shared characteristics.

In the first implementation, the group that said individual falls into (defined by age and/or any other characteristic or condition that would cause the optical quality of the eye to change) and previous measurements and analysis of the image quality of others who fall within the same group are used to determine one or more of the optimum instrument pupil size, pupil position, pinhole size in front of the detector and/or wavelength which will result in the best quality of an image of the retina or fundus. For one image quality variable (lateral resolution), using prior optical measurements on a large number of eyes, stratified as a function of age, we show the methods by which the optimum instrument pupil size optimum pupil centration and optimum pinhole size in front of a detector in a system built to image the retina, can be found as a function of age, the wavelength of light, pupil size and pupil centration.

In conditions such as diabetes in which the optical properties of the eye change and there is evidence that the optical aberrations increase (Valeshaba, 2014), we teach following the same procedures as above to determine the optimum conditions for imaging as a function of any variable describing the disease which in turn affects image quality. We present the methodology by which we establish data from which the best optical image quality and correspondingly one or more of optimum pupil size, pupil size centration, detector pinhole size and/or wavelength of light at which it occurs can be determined for individuals, having characteristics similar to the initial group measured, as a function of one or more of age and ocular or systemic condition.

As an example of optimizing the quality of retinal images for a specific group, from prior optical measurements on a large number of eyes (1200), stratified as a function of age, we have shown that both the optimum pupil size and by extension pupil centration and optimum pinhole size in front of a detector in a system built to image the retina, differ as a function of age and wavelength. Herein we teach that once the calculations have been performed across a large number of individuals of varying age, the best optical image quality and optimum pupil size at which it occurs can be chosen to be the same for any individual who shares characteristics with the initial group measured, in this case age. In a similar manner, the optimal pupil centration and optimum pinhole size in front of a detector in a system built to image the retina as a function of wavelength and the severity of the condition.

As we teach herein, when an individual has a known condition (such as diabetes or the presence of cataract in which the optical properties of the eye change, with the severity and/or duration of the condition), the same methodology can be applied to derive optimum settings for the pupil size, centration and the detector pinhole size. We have established the optimum pupil size for those with diabetes as a function of diabetes duration. By extension by the methods outlined the optimal pupil centration and detector pinhole size could be found. We have also shown the dependence of the optimal image quality on the wavelength of light.

In the first methodological implementation, as described above to determine optimal conditions for the eye of an individual, the imaging conditions for improved image quality are chosen on the basis of the group that said individual falls into, including groups with specific ranges of ages or specific conditions that cause changes in the optical quality of the eye. As well as resulting in improved images of the retina and or fundus, the methods described may also result in improved vision for the individual, dependent on an intact retina and visual system.

In the second implementation of these methods to improve the quality of the image of the retina, optimum values of imaging parameters (eg pupil size) are determined directly for an individual. The particular optical properties of the individual's eye that is the wavefront errors are measured either prior to or during the imaging session. Then one or more of the optimum pupil size, pupil centre position, detector pinhole size and/or wavelength which gives the best quality of the image is determined and then implemented. This may be determined by a detailed calculation given the individual's wavefront errors by the phase plate approach described above. A calculation of a given image quality metric can then be made for an individual for whom the wavefront aberrations have been measured, as a function of one of pupil size, pupil centre position, or wavelength. The optimum value of the chosen variable (say pupil size) is the value for which the chosen image quality metric is best (eg the lowest value of lateral resolution.)

One way a more rapid calculation can be made of optimum pupil size for a given image quality metric for an individual whose wavefront errors have been measured is if an overall metric of image quality of individuals within a group for example the RMS of the wavefront error of individuals at a larger pupil size (5 mm in FIG. 7 for normal individuals) has been plotted as a function of an optimum variable (pupil size in FIG. 7 or pupil position, detector pinhole size and/or wavelength) for a given metric (in FIG. 7 for encircled energy). From such a plot, for a given RMS, one can read off the optimum pupil size or other optimum variable.

We further show how the above methods allow the optimization of the pupil size, pupil centration, detector pinhole size and/or the wavelength of light for the improvement of the images, usually for central vision (at or close to the fovea) but also potentially for additional locations on the retina, at which the optical quality of the group of which the individual is a member has been measured or for which the individual's wavefront has been measured. We then teach that the methods described can be extended to the quality of images acquired either at other locations on the retina where imaging is deemed desirable or simultaneously at multiple locations on the retina.

This intellectual property also describes the apparatus and methods that allow the images taken for a range of wavelengths of light to be improved from measurements taken using a different wavelength of light. The intellectual property also discloses methods and apparatus for determining, at the wavelength(s), optimum pupil sizes and positions and pinhole sizes combined to given improved image quality on the retina.

In addition, more specifically, this intellectual property discloses methods and apparatus for measurements and calculations of the resultant image quality of eyes as a function of the size and/or decentration of the pupil of the eye as well as a function of wavelength, from optical properties measured for a given individual or from the known properties of the eyes of a group into which said individual falls. These properties may include detailed measurements of the deviation of light from its ideal path across the pupil of the eye (also known as wavefront aberrations), the quality of the image formed on the retina for different imaging configurations described by for example a point spread function or the modulation (and potentially the phase) transfer functions or described by a metric of image quality that summarizes either of these two measures. The calculations of image quality above may also be made on a model of the eye created for the individual as described herein or from a model known to describe the optics of eyes of a group to which the individual belongs where such group may be defined by parameters including one or more of age, gender and ocular or systemic conditions.

The calculated variation of image quality is in turn used to determine one or more of the ideal pupil size, pupil centration and wavelength of light which gives the optimal image quality in retinal images for the features which are desired to have best quality. Thus, this intellectual property discloses methods for improving the resolution of features on the retina as well as for improving the overall contrast of features or the contrast of features of a specific size as a function of one or more of wavelength pupil size and/or pupil position. This in turn allows overall improved images as well as the detection of particular features associated with conditions or diseases, the detection of which may be the goal of taking said images.

The present disclosure provides a method for improving optical images of the retina or fundus, comprising the steps of:
 a) choosing a wavelength of light for imaging
 b) focusing the instrument on the feature of interest on the retina/fundus
 c) deciding what metric of image quality resulting from imaging through the optics of the eye is most important to the purpose of imaging the retina or a portion of the retina (eg lateral versus depth resolution versus overall image quality metrics versus the contrast of features of a particular size);
 d) choosing an additional parameter or parameter(s) to be adjusted as one or more of pupil size, pupil centration, and/or detector pinhole size;
 e) determining which group(s) the individual falls into where the property defining said group(s) or subgroup(s) is known or suspected to change the optical quality of the eye and in turn the best values of the adjustable parameter(s) on the instrument and where groups may include but are not limited to one or more of age, the presence of diabetes, and the presence of cataract or pre-cataract.
 f) with knowledge of the overall optical quality as described by the magnitude of the wavefront aberrations across the pupil of an individual's eye or of the eyes of a group into which the individual falls, consult the previously calculated value of an adjustable parameter of the fundus imaging system that will give the best value of the metric chosen in b) or estimate from the RMS of the wavefront aberration of individual the value of the adjustable parameter that will give the best value of that metric or calculate from the wavefront aberrations of the individual the value of the adjustable parameter that will give the best value of that metric;

g) adjust the adjustable parameter of the instrument in c)
h) repeat d) e) and f) for other adjustable parameters
i) perform a visual check of perceived image quality to determine any final adjustments.

A further understanding of the functional and advantageous aspects of the present disclosure can be realized by reference to the following detailed description and drawings.

DETAILED DESCRIPTION

Figure 1:
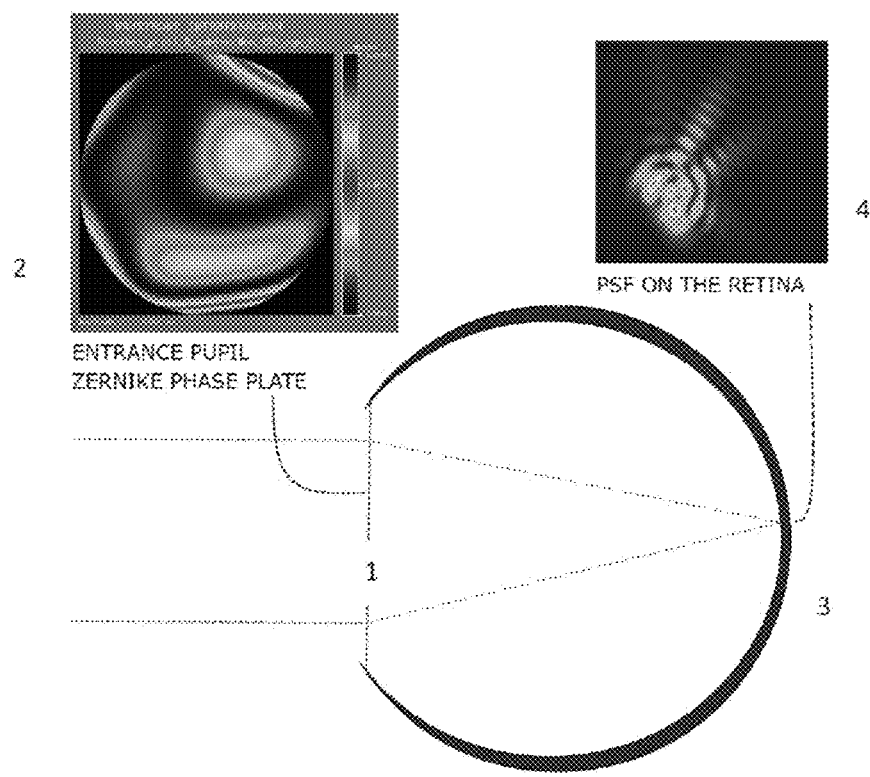
FIG. 1 is a diagram of the preferred implementation of a calculation of the ideal pupil size, pupil position and ideal wavelength. Measured higher order aberrations from the measured Zernike coefficients are placed in the plane of the entrance pupil of the eye as a phase plate (1). A schematic of a sample phase plate representing the higher order aberrations is given (2). The image quality given by a point spread function or by a modulation transfer function (MTF) is then calculated on the retina (3) for a particular angle of entrance of the beam to the presumed optical axis of the eye using a paraxial eye model. This angle describes the region of interest for imaging the retina. A sample calculated PSF is given (4). In our preferred implementation, the calculation is made using an optical design program. The PSF or MTF is calculated as a function of one or a combination of pupil size, pupil position detector pinhole size and/or wavelength, A metric of image quality applied to either the PSF (for example the diameter of the 50% encircled energy as an estimate of lateral resolution) or the MTF is calculated for each of the variable combination. The value of the variable (for example pupil size) that gives the best value of the metric (for example lateral resolution can then be found (see FIG. 2).

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

The present disclosure provides:

A) Methodology for Improving Image Quality by Establishing the Optimum Instrument Parameters, Wavelength:

When varying wavelength in an optical imaging system which is diffraction limited spot size and the resolution of the systems gets larger (poorer) proportional to the increase in the wavelength of light from the visible to the infrared. But the eye suffers from aberrations in monochromatic light which have been shown by a variety of authors to remain almost constant when measured in microns as a function of the wavelength of light (Marcos, 1999; Fernandez, 2008, Bueno, 2010). Starting with our dataset of higher order monochromatic aberrations in normal eyes at 550 nm, we modelled the monochromatic aberrations as constant with wavelength, at a variety of pupil sizes (see pupil section for details). We derived values of aberrations at two additional longer wavelengths. We then calculated retinal point spread functions and associated image quality metrics as a function of pupil size and wavelength. For small diffraction limited pupil sizes, the radius of 50% encircled energy (a metric of lateral resolution) increased by the ratio of the wavelengths as well known in diffraction limited systems. However, above a 3.35 mm pupil diameter, the radius of 50% encircled energy and resolution remain constant with increasing wavelength. The optimal pupil size was less than 3.35 mm and greater than the diffraction limit. As we increased the wavelength, on average, the optimum pupil size (corresponding to the best resolution, see part B) increased as did the corresponding best lateral resolution, getting worse with increasing wavelength from an optimum pupil size of 2.7 mm at 550 nm (with a resolution of 4.5 microns) to an optimum pupil size of 3.1 mm at 830 nm (with a resolution of 5.9 microns).

Figures 5, 6:
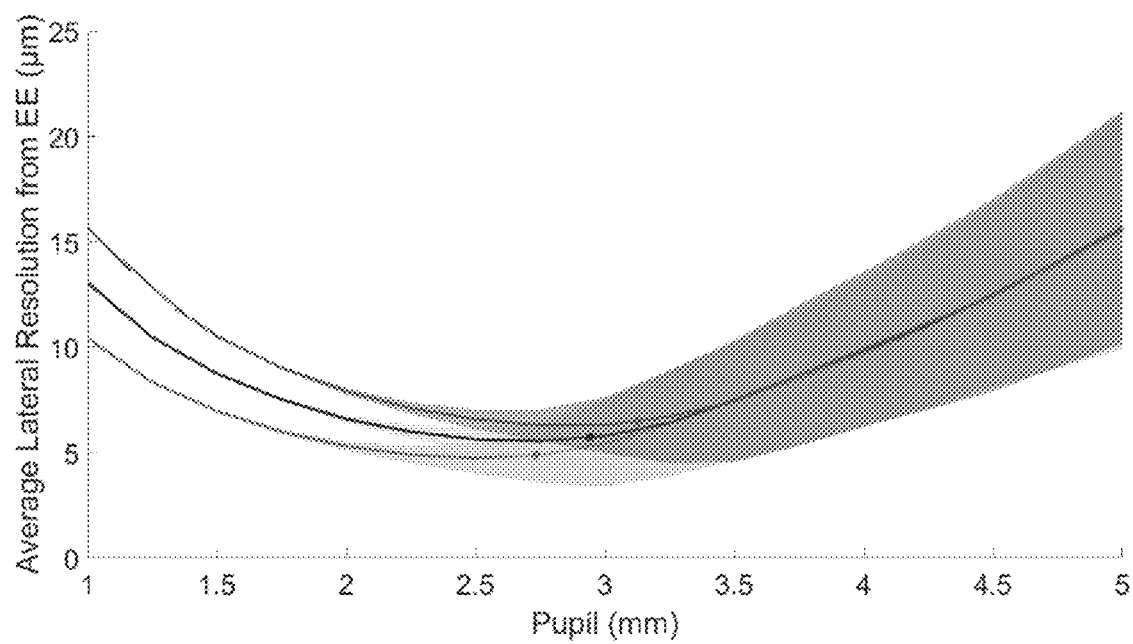
FIG. 5 gives the averages and standard deviations of the optimum pupil size (OPS) in mm and the corresponding lateral resolution (LR) in microns for normal individuals in the age range 58 to 70 years at a wavelength of 830 nm. The lateral resolution of 5.9 microns is somewhat worse that the 4.48 microns at 550 nm (FIG. 3) but the decrease is less than the 50% decrease predicted by the wavelength change. And the corresponding optimum pupil size in the infrared (3.13 mm) versus 2.73 mm at 550 nm provides the first evidence of an additional advantage of the use of infrared light. That is the larger pupil in the infrared gives a similar resolution to that of a smaller pupil at a 550 nm wavelength.
FIG. 6 plots the average lateral resolution taken from the radius of the 50% encircled energy of the point spread function in microns versus the pupil diameter in mm for normal individuals 58-70 years old with differing wavelengths of illumination. The lowest, middle and top curves correspond to a 550 nm, 690 nm and 830 nm imaging wavelengths, respectively (see also FIG. 5). The shading around the curves indicates the standard deviation across the individuals in the group. On each curve, the dots mark the optimum pupil size that gives the best lateral resolution for that wavelength of illumination and the corresponding best lateral resolution. As the wavelength increases from 550 nm to 690 nm to 830 nm, the optimal pupil size gets larger and the resolution on average decreases somewhat but less than the ratio of the wavelengths. However, the spread across individuals increases.

However, the decrease in resolution of 30% between the two wavelengths is much less than the 50% in the diffraction limit. Moreover, when imaging with pupils larger than 3.45 mm, the image quality is independent of wavelength. This is a novel result which points to advantages of imaging with infrared light (FIG. 6). There may however be more scattered light from deeper in the retina in infrared light (Bueno, 2010).

A1) Optimum Wavelength Choice for Images of the Retina and Corresponding Image Quality as a Function of Wavelength (and Pupil Size)

For optical systems without aberrations or for systems with aberrations but when small enough pupils are used, it is known that the blur on the retina, lateral resolution and most other image quality metrics get worse at longer wavelengths, as a result of the direct linear dependence of the radius of the point spread function (PSF) on the wavelength of light used in the imaging. So, in this situation, the image quality metrics are expected to worsen proportional to the wavelength of light used for imaging.

Firstly, we apply the methods also described below for finding the best pupil size of 1) finding from the HOAs measured at one wavelength using established methods, those at a different wavelength, 2) using a phase plate representing the HOAs to calculate the PSF or MTF as a function of pupil size, we find the optimum pupil size which gives the best image quality for imaging at each wavelength for each individual eye in given age group and 3) we average the results we find at each wavelength across the individuals within a given age group. 4) We calculate the average of the chosen image quality metric, for example the radius of 50% encircled energy representing lateral resolution.

We find that moving to longer from shorter wavelengths produces as much image degradation as predicted above from the assumption of diffraction, only for smaller pupil sizes. For example we have shown that for the oldest age group we considered (58-70 years) and for smaller pupil sizes below 2.5 mm, the radius of the 50% encircled energy (a measure of lateral resolution) at the optimum pupil size in each case, increased approximately 50% when the HOAs were converted using established techniques from 550 nm to 830 nm and image quality metrics and optimum pupils were calculated as previously described. This is close to the result predicted by the size of the diffraction spot (with no HOAs) in the two cases (51%).

However, we found that moving to longer from shorter wavelengths produces much less image degradation than predicted above from diffraction, when, at both wavelengths considered, the optimum pupil size for lateral resolution (see detailed methods in part B) was larger than 2.5 mm. In the older individuals, at these larger pupil sizes including at the optimum pupil sizes for lateral resolution at the two wavelengths, best lateral resolution only dropped by 30% when moving to 830 nm from 550 nm (from 4.5 microns, optimum pupil of 2.73 mm at 550 nm (FIG. 3) to 5.9 microns, optimum pupil 3.13 mm at 830 nm (FIG. 5).

Furthermore, at pupil sizes above 3.45 mm, with the HOAs of older eyes, the radius of 50% encircled energy and resolution remained relatively constant with wavelength at a given pupil size (eg 7.2 microns for a 3.45 mm pupil) for wavelengths from 550 to 830 nm. In some eyes at larger pupils, resolution at 830 nm exceeded that at 550 nm (FIG. 6).

These results, for higher resolution at longer wavelengths compared to shorter wavelengths than expected in the absence of wavefront aberrations, are important to the design of ophthalmic instruments for imaging the retina. We have shown, for the first time, that image quality when imaging the retina in infrared light at some pupil sizes in the presence of the HOAs in older eyes, is actually better than when imaging at visible wavelengths.

There are numerous known advantages of imaging the retina and fundus at longer wavelengths, including the higher allowable safe light intensities, comfort for the individual, reduced need for pupil dilation with topical agents, and the potential to produce two photon excitation of intrinsic fluorophores. One primary assumed disadvantage of imaging at longer wavelengths is the reduced resolution of retinal features compared to visible wavelengths. The fact that resolution at longer wavelengths at optimum pupils which produce the best metric of image quality shows a slower degradation with increasing wavelength than in the absence of aberrations is likely to make imaging in the infrared even more advantageous (See lateral resolution as a function of wavelength for the older age group in FIG. 6, Table 2). An added advantage of imaging in IR light is the larger optimum pupil size for 830 nm illumination. This allows more light to be incident on the retina and potentially produces brighter images. This analysis for optimum pupil size as a function of wavelength can be repeated for any age group. However, these findings suggest that one should start with an infrared wavelength when imagine the retina and fundus of the eye.

In summary, in the eye, image quality decreases with increasing wavelength, less than predicted by diffraction because HOAs change little with wavelength. Imaging with infrared (IR) light at a pupil size that gives optimal resolution causes a reduction in image quality compared to visible light which is smaller than in the absence of HOAs. At larger pupils, image quality in IR is similar to that in visible light, also due to the low dependence of HOAs on wavelength. This improved resolution, along with the advantages of patient comfort and higher safe levels of illumination, make IR illumination an even better choice.

B) Once the wavelength for imaging is decided, methodology for improving image quality by establishing the optimum instrument parameters (one or more of pupil size, pupil centration, detector pinhole diameter and) for improved images of the retina as a function of the groups that the individual falls into including to which age group they belong; the imaging instrument used and any changes from normal in ocular properties of the eye due to any condition that the individual has that would have altered the optics from normal reg diabetes, cataract, refractive surgery, lens implants and any others). However, note that the optimum pupil size can be found for any wavelength chosen for imaging.

Firstly, one should decide on the image quality metric that one wishes to optimize where the choices include but are not limited to lateral resolution, depth resolution, Strehl ratio, area under the MTF, Hopkin's ratio, the contrast at a particular spatial frequency or range of spatial frequencies or any others, known to those skilled in the art.

1) Improved quality of the images of the retina will be accomplished by a particular choice of one or more of wavelength, pupil size and pupil centration and detector pinhole size on the basis of previous analysis pinpointing the optimum values for the group an individual falls into where this group can be defined by age and/or by the presence of an ocular condition known to change the optical quality of the eye:

a) The analysis of the optimum pupil size and optimum pupil position and the optimum pinhole size and corresponding best image quality for each parameter at one wavelength for eyes as a function of age without additional conditions which affect the optics of the eye: Given the previously measured ocular aberrations for a group to which an individual belongs or from measurements of that individual at a particular wavelength, we present a method for 1) calculating image quality as a function of pupil size for a given wavelength. This is accomplished by 2) Calculating the image quality as a function of pupil centration and 3) determining which combinations of wavelength, pupil size, pupil centration, will give better images of the retina, given certain other considerations, in particular, the desire to choose a wavelength for patient comfort. 4) Determining the optimum chose of detector pinhole size.

We started with a previously published large dataset of measured higher order wavefront aberrations (HOAs) for individuals with a large range of ages at a single wavelength. The variable of age could be replaced by any other variable of interest, say that of a condition of the eye affecting optical quality which can be stratified with a metric of severity (for example diabetes as a function of disease duration or cataract as a function of severity grade). The methodology would remain unchanged if more data became available to increase the total dataset of eye measurements at different wavelengths, ages and/or conditions. In the literature, almost constant HOAs as a function of wavelength have been previously measured. Methods have also been previously described to convert the aberrations at a given wavelength to those at additional wavelengths. The calculation of the image quality of an eye uses a phase plate with a paraxial eye model which has been previously described.

In our novel methodology, 1) initial eye models Mere created from the HOAs of individual eyes in the large dataset,
  2) then stratified into a given age range at the wavelength and pupil size at which the HOAs were measured.
  3) Then the HOAs were recalculated at differing wavelengths and described for smaller pupil sizes using known methods.
  4) The thousands of phase plates of HOAs (FIG. 1) corresponding to the data set of eyes recalculated at different wavelengths and pupil sizes, were then each combined with a paraxial eye model. In more general application, this can either be an average eye model with one focal length or one with a focal length which varies with age or ocular condition.

5) Various quantities (including the point spread function on the retina (FIG. 1), the modulation transfer function (MTF) and corresponding metrics of retinal image quality derived from each of these were then calculated, using known methods (in our implementation, by interfacing to a commercial optical design program), as a function of pupil size and wavelength for each individual. The calculation can also be extended as a function of pupil position.
6) Many known or new metrics of image quality are next calculated. In our implementation, these were measures of resolution (lateral resolution: the radius of 50% encircled energy and depth resolution), and the cut-off spatial frequency, as well as the contrast of features of a particular size, determined by reading the value of the modulation transfer function at a spatial frequency, predominant in a given feature, and the Hopkins ratio which is a global image quality metric and increases as the volume under the MTF increases. Other known metrics of image quality can also be used.

The above calculation is made for a single pass of light into the eye. However, the image quality calculated on the retina is in turn the image quality produced in the image given by the instrument if the instrument is set up so that it gives the same image quality as that given in a single pass through the optics of the eye (apart from a magnification factor and assuming adequate sampling of the image). Practitioners practiced in the art of constructing optical instruments for imaging the retina (and/or fundus) know the configurations that produce the quality in the image which is the same as that given by forming an image on the retina. In fundus cameras, this is often the exit pupil of the instrument through which light reflects from the retina. In that design, the illumination enters through an outer annulus which does not influence the quality of the retinal image. The exit pupil is then the one for which we wish to define size and centration to give best retinal image quality.

In a scanning laser ophthalmoscope, light normally enters a moderately sized pupil (whose size and centration we wish to define to give the best retinal image quality. The reflected light exits through a large pupil which does not affect the quality of the retinal image.

Herein, we wish to define a novel configuration for a scanning laser ophthalmoscope of particular applicability to imaging older eyes. The light path onto the retina is through a relatively small entrance pupil (~2 mm) which gives a large point spread function on the retina. The light returning to the instrument from the retina then exits through a pupil size defined to maximize the image quality metric of choice. This will be larger enough than a 2 mm pupil (at least 3 mm, dependent on age) and to give the primary contribution to the resulting quality of the image of the retina. This has the advantage of collecting light through the larger of the two pupils and allows imaging in older individuals in whom you would need to use dilation drops to produce the large exit pupil in the traditional configuration.

In each of the pupil configurations described above, the final image viewed with the instrument will then be blurred by the single pass point spread function and will differ in feature size only by the magnification of the retina (or fundus) imaging instrument.

In the following image quality is discussed in terms of the point spread function (PSF) and as an example, the size of 50% encircled energy on the retina (a well-known metric of resolution). The same methodology applies if a different metric of image quality (either derived the from the PSF or from the modulation transfer function (MTF) is used. The methods of optimizing retinal image quality for the purpose of improved imaging would also apply to any situation in which an individual views objects through particular pupils (for example in instruments used with the eye and attempts to find the optimum pupil for said instrument).

After step 6) described above calculating image quality and its metrics, in step 7) we then determine at a particular wavelength for each individual, the conditions for imaging (optimum instrument imaging settings) (one or more of pupil size, pupil centration, detector pinhole size or wavelength) that gave the best retinal image quality. The resulting values of settings from individual eyes across a given age group with a small age range were averaged together to give the optimum settings for that group. The resulting values of an image quality metric were also averaged as an indicator of performance at a given age.

Figures 2, 3:
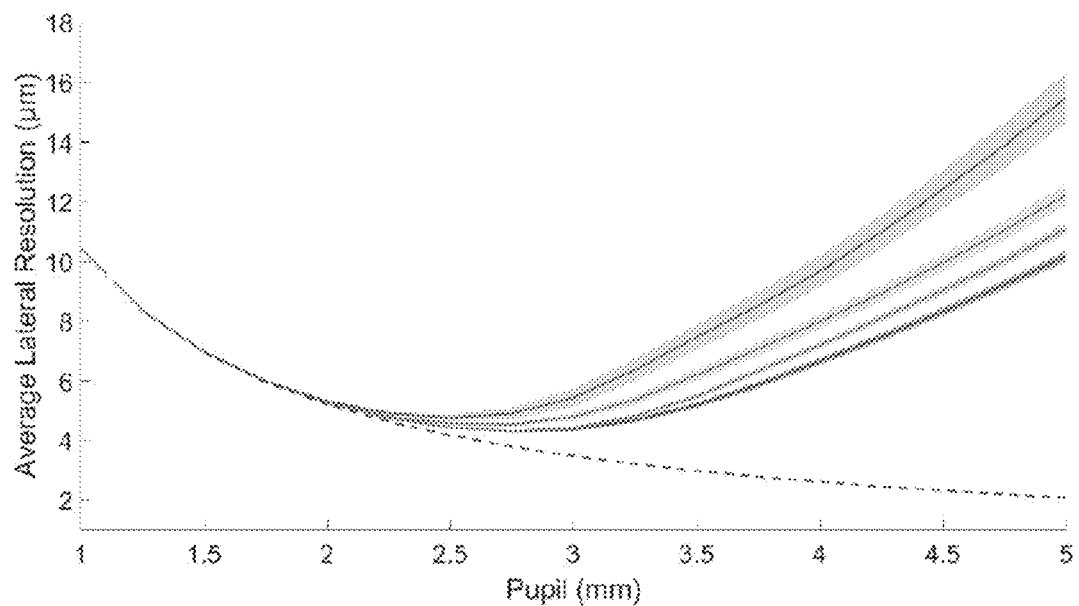
FIG. 2 is a plot of the average lateral resolution in microns taken from the radius of a circle encompassing 50% encircled energy of the point spread function for light at 550 nm versus the entrance pupil diameter in mm. The averages are given by the solid lines and are taken across members of a differing age groups. The grey area around the line is the standard deviation of the values for the group. The minimum value of any one curve represents the best lateral resolution for the corresponding optimum (optimal) pupil size. Different curves are for different age groups. The dashed line is lateral resolution in microns versus pupil size in mm when there are no aberrations present. The paraxial eye model then focusses the light onto the retina. The curve closest to the dotted curve is for the 20 to 32 years old croup, the next curve is for 33 to 45 years old; then 46 to 57 years old and finally 58 to 70 years old. In each case the corresponding best lateral resolution and the optimal pupil size giving that resolution can be read from the minimum of the curve.
FIG. 3 is a table of optimal pupil sizes (OPS) in mm and the corresponding best lateral resolution (LR) in microns for light at 550 nm read from the curves in FIG. 2 for each of two age groups, the 20 to 32 years old group on the left and the 58 to year 70 years old group on the right.

In one sample implementation, we calculated the optimum pupil size for groups of participants as a function of age and using a metric of average lateral resolution, the 50% encircled energy in the PSF. The pupil size giving the best image quality from the value of the image quality metric (for encircled energy, the smallest value, a measure of lateral resolution). We also calculated the resulting best image quality. From this work, we found that the optimum pupil size for resolution decreased as a function of the age group plotted (FIG. 2). The optimum pupil size was a function of the image quality metric chosen Metrics are chosen dependent on the retinal feature of main interest. As an example, in a situation where resolving small retinal features is important, the metric chosen was lateral resolution. Other metrics of image quality can be chosen by one skilled in the art and with knowledge of the image quality most important when imaging particular retinal features.

FIG. 3 contrasts the optimum pupil size and the resulting best lateral resolution for individuals 20-32 years old with those for individuals 58-70 years old at 550 nm. Thus, using the outcomes from this methodology, the optimum pupil size can be adjusted to these averages, or the averages for other age ranges, dependent on the age group of the person being imaged.

From the results, for a given wavelength of light, the average lateral resolution was a function of age and pupil size (FIGS. 2, 3). The optimum pupil size at which the lateral resolution was minimum (best) shown here for 550 nm wavelength was different for different age groups, decreasing as age increased. The best lateral resolution also increased (worsened) with age. From the results obtained, for a given wavelength, this analysis allows us to specify the optimum pupil size for imaging the retina to achieve the best value of a given metric of image quality on the basis only of the age of the individual as long as they do not also suffer from a condition known to alter the optical quality of the eye (for example diabetes).

The methods outlined here can be extended to other applications, including the optimum pupil size for a number of other image quality metrics which may be important to the features of interest in the retinal image. For example, for amyloid deposits in the retina which often have small sizes, not resolvable in retinal imaging. But some have sizes as large as 15 microns and larger. From a consideration of the MTF, one can adjust the pupil size to give the highest contrast for features of the approximate size of interest by optimizing the MTF (and contrast of said features) at the corresponding spatial frequency. Any other metrics of image quality, familiar to a practitioner in the field may also be used as appropriate in relation to the size and contrast of the feature(s) of importance being imaged.

Figure 4:
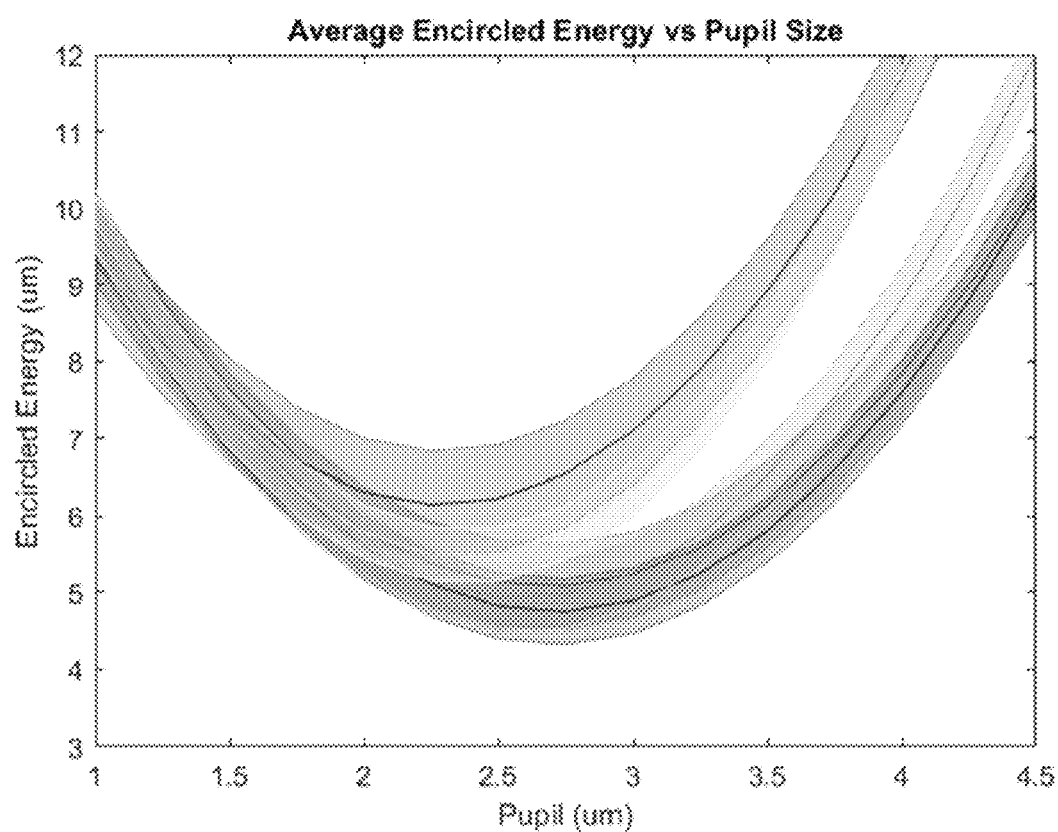
FIG. 4 is a plot of the average of the radius of the circle encircling 50% of the light energy of the point spread function for light at 550 nm (labelled encircled energy) in microns, for individuals with diabetes. This corresponds to the lateral resolution in microns versus the entrance pupil diameter in mm. The averages are given by the solid lines and are taken across individuals with differing durations of the disease (diabetes duration). The grey area around the line is the standard deviation of the values a group with a small range of durations. The minimum value of any one curve represents the best lateral resolution for the corresponding optimum (optimal) pupil size. Different curves are for different groupings of diabetes duration. The curve furthest to the right is for a diabetes duration of 3-10 years, the curve to the left of it is for a diabetes duration of 10-14 years, the next curve is for a diabetes duration of 14-19 years, the next curve is for is for a diabetes duration of 20-29 years and the final curve is for a diabetes duration of 30 to 44 years old. In each case the corresponding best lateral resolution and the optimal pupil size giving that resolution can be read from the minimum of the curve. Note that as diabetes duration increases, the best lateral resolution attainable increases (gets worse) and the pupil that gives the best lateral resolution decreases. For the longest diabetes duration, the resolution is poorer than for the oldest normal individuals and the optimal pupil size is smaller than for the oldest individuals in FIG. 3.

This process has also been repeated step by step (1-7) above for the eyes of group of participants with diabetes whose wavefront aberrations had been measured. It was found that metrics of image quality became worse as the length of time from diagnosis of the disease (diabetes duration) increased. It was also shown that the optimum pupil size decreased (from 2.75 mm for 3-10 years to 2.25 mm for a duration of 30-44 years as shown with increasing diabetes duration (FIG. 4). This methodology could be extended to any other conditions known to adversely affect the optical quality of the eye. We expect to find similar relationships of decreasing optimum pupil size with other markers of diabetes, including HbA1c and crystalline lens thickness. For a large enough data sets we expect that there might be an optimal pupil size for a given individual which depended both on one or more markers of their disease (eg diabetes duration, blood marker HbA1c and/or crystalline lens thickness) and simultaneously on age.

From the methods outlined, the optimum pupa size and corresponding lateral resolution or any other chosen metric can be predicted dependent on the wavelength used for imaging, the age of the individual being imaged and/or the severity of the ocular condition of the individual. Besides the change in optimum pupil size, the trade-off between loss of resolution and other advantages of illumination at longer versus shorter wavelengths, can be explicitly considered using the methods outlined above.

All of the methods, outlined above, can be extended to any metric of image quality, any particular wavelengths and any age grouping of individuals, including curves of optimum pupil size as a function of age for individuals at different wavelengths. Additional measurements of HOAs either on more participants or at a wider range of wavelengths when available can be incorporated into the analysis. Optimum pupil size that proves the quality of images of the retina and corresponding best image quality as a function of wavelength for eyes in a certain age group with additional conditions which affect the optics of the eye: For individuals with conditions which affect the optical quality of the eye, often causing larger higher order aberrations than in eyes without the condition, (for example in diabetes and cataract), all of the methods outlined above can be extended to consideration of the optimum pupil size to give best image quality as defined by a metric of image quality, for imaging, now using the measured HOAs averaged across individual eyes with said condition. The methods outlined can also be extended to the evaluation of image quality in eyes where either the measure of HOAs or any other ocular measurements can be evaluated for the presence of scattered light, using established methods. The effects of this scattered light can then be modelled using an additional element with approximately the same resulting scattering on the retina in the model eye to that which was measured. Image quality metrics and optimum pupil sizes can then be evaluated as described above.

B1) We start with one established method, that of wavefront sensing. This produces a measure for an individual of the higher order aberrations. On the basis of this measurement, we can then proceed to calculate the optimal pupil size, optimal detector pinhole size and effects of different wavelengths of light using the steps outlined in A) and applied to this individual. The calculation can be undertaken for any particular image quality metric desired.

B2) We can simplify and speed up the determination of the optimum pupil size so that gives the best value of any image quality metric chosen by using a single value descriptor of the higher order wavefront aberrations (HOAs), in particular, the root mean square value (or RMS value) for an individual calculated across the pupil for which they were measured. From the RMS value, we then predict the optimum pupil size for a given image quality metric, based on our prior extensive calculations on a larger population which showed the novel result that the optimum pupil size for a given image quality metric showed a highly significant dependence on the RMS of HOAs (FIG. 5). Once the optimum pupil size has been calculated for a specific wavelength, that for other wavelengths can be calculated as previously described.

C) Optimum (Optimal) Pupil Centration:

Once the optimum pupil size has been found from the larger pupil for which the wavefront aberrations were calculated, this pupil has by default the same centration as the larger pupil. Significant shifts of the pupil centre with respect to a reference axis of the eye of up to 0.6 mm have been shown for changes in pupil size with illumination (Wilson 1992). Thus, a calculation of the image quality metric of interest for a pupil of optimum size, with optimum pupil centration can be made following the description of finding the optimum pupil size. Finding the optimal (optimum) centration for imaging involves moving the optimum pupil size across the wavefront aberration map in the horizontal direct in increments of ±0.1 mm over 0.6 mm in first the horizontal, finding the optimal position and then moving in the vertical direction in increments of ±0.1 mm over 0.6 mm. The methods following in calculating the best value of the chosen image quality metric as a function of the centre of the pupil to be used for imaging follows the same procedure as calculating the best value of the chosen image metric as a function of pupil size. This may be determined by a detailed calculation given the individual's wavefront errors by the phase plate approach described above. If the value of the metric of interest calculated across the visible wavefront error gets worse, then the opposite direction of motion can be tested. One needs to mark the optimum pupil centre in relation to the centre of the pupil of the original higher order wavefront aberration map. This can be done at the time that the original wavefront aberration map was taken by measuring the centre of the pupil through which that map was taken with respect to a landmark on the iris or a reflection from the cornea or any other ocular reference including the subjective location of the achromatic axis of the eye (Simonet, 1990; Thibos, 1990; Wilson, 1992). In exploring the optimum centration of the pupil of optimum size, the achromatic axis of the eye can be used or an aperture surrounded by an infrared filter illuminated in infrared light, giving an image on an infrared camera, would allow e location of the centre of the optimum pupil relative to the centre of the original pupil over which the wavefront aberration were measured to be located relative to the landmarks. The steps of determining the centre of the artificial pupil which gives the best value of the chosen image quality metric uses the same steps as the process of determining the optimum (optimal) pupil size and the corresponding value of the chosen metric. This involves a detailed calculation of image quality given the individual's wavefront errors behind the moving aperture by the phase plate approach described above.

Detailed steps are: in order to determine the optimum centration of the pupil with respect to the pupil for which the wavefront aberrations were measured, use an aperture the size of the optimum pupil surrounded by a filter opaque to visible light but which allows the illumination of the ocular structures surrounding the pupil in infrared light; then use as a reference to locate the movable pupil with respect to the original pupil centre which is not limited to one of a) a landmark on the retina, b) a reflection associated with an ocular component, for example the first Purkinge image which is a reflection from the cornea or c) the subjective achromatic axis of the eye; then follow the steps of moving the optimum pupil size across the wavefront aberration map in the horizontal direction in increments of ±0.1 mm over 0.6 mm in first the horizontal, finding the optimal position and then moving in the vertical direction in increments of ±0.1 mm over 0.6 mm. where for each position the value of the chosen image quality metric is calculated and the best value is found following the same procedure as calculating the best value of the chosen image metric as a function of pupil size where if the value of the metric of interest calculated across the wavefront error for a particular pupil centration gets worse, then the opposite direction of placement of the pupil centre can be tested.

D) Optimal Detector Pinhole Size Depends on Optimum Pupil Size:

In the literature, (LaRocca, 2013) have identified what they described as optimal pinholes to be placed in front of a detector to optimise the trade-off between the throughput of light and the resolution of the detector for a particular, young subject. This is dependent on the projection of the PSF of the eye onto the detector. That point spread function in turn is a function of instrument pupil size. If one is using an optimal pupil for resolution, the PSF at the detector will be minimized.

To be more explicit in the aim of the pinhole, it is to allow throughput of the central part of the PSF and to reduce contributions from the wider-angle area of the PSF, assumed to be due to scattered light. This will in turn increase the contrast of the retinal image. So once the optimum pupil size has been determined across a subgroup of individuals defined by the group they fall into and a value within that group (eg normal with age as the value or those with diabetes with diabetes duration as the group), we have the optimum pupil size and its standard deviation for the group as a function of a value (eg age or diabetes duration). Then the steps to be followed to determine the optimum pinhole are for each value within the group are:

1) For the optimum pupil size for each individual, if not previously calculated, calculate the image quality metric of 50% encircled energy of the point spread function and take this value times two as an estimate of the diameter of the central area of the PSF; 2) Repeat the calculation for the 70% encircled energy to get a second, larger estimate of the diameter of the central area; 3) Take the averages and standard deviations of the values in 1) and 2) across the group of individuals for the value of a particular descriptor (for example age or diabetes duration); where the resulting values are estimates of the sizes as projected onto the retina of the minimum and maximum pinhole diameters to be explored; 4) if the wish is to emphasize depth resolution, set the diameter of the pinhole to between 2 and 3 times the diameter estimated of the central area of the PSF from 50% encircled energy; 5) If the wish is to improve the contrast of the image by excluding scattered light, at low power, hold the scanning beam stationary initially while the beam illuminates the centre of the desired imaging area on the retina and determine the intensity of the light captured before and after the pinhole is adjusted to the two sizes (corresponding to 50% and 70% encircled energy where if there is little change in intensity between the diameters given by 70% and 50% values, use the diameter from 50% encircled energy; otherwise use the 70% value; 6) and in eyes known to have larger amounts of scattered light (older and/or other conditions), if the light intensity goes up substantially between the smaller and larger pinhole diameters, use the larger value; 7) then after placing the beam back in scanning beam mode, compare the brightness and contrast of the image before and after the insertion of the pinhole and/or as the pinhole diameter is adjusted by small amounts; and 8) choose a pinhole diameter which gives a high contrast image which has a full range of intensities as sampled by the detector; then 8) If desired, steps 1) to 7) may be repeated for midperipheral and peripheral features of interest on the retina a value of the pinhole may be chosen which gives acceptable brightness and contrast for all three positions.

Preferred Implementation

Figure 8:
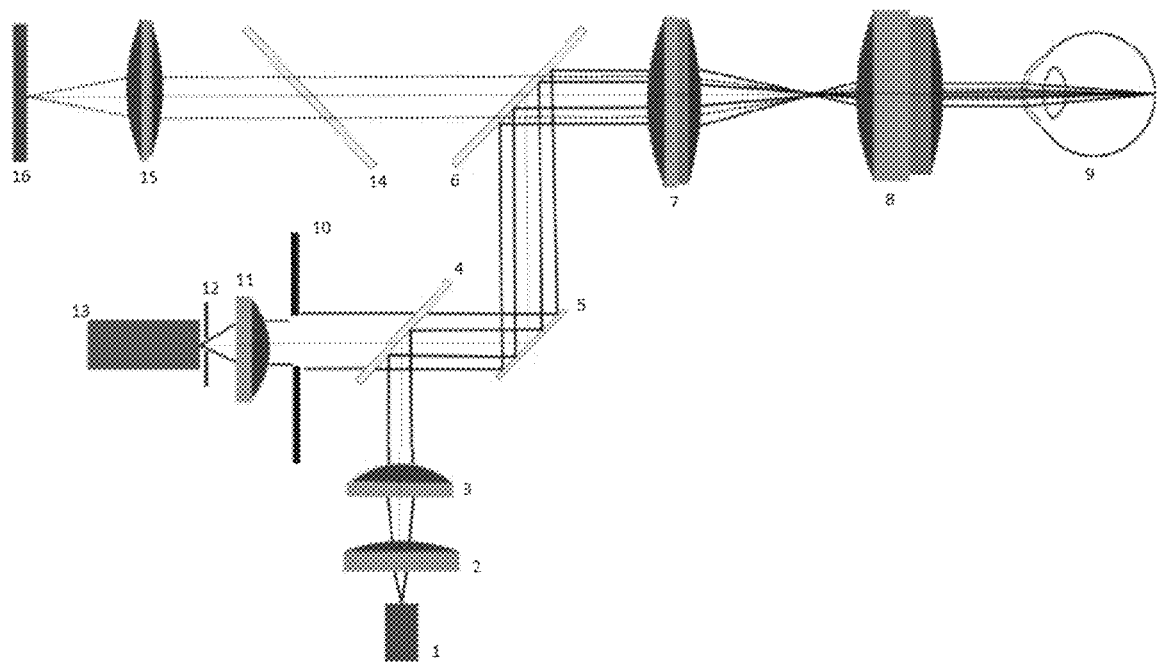
FIG. 8 gives the preferred implementation of the retinal (fundus) imaging system for improved image quality where 1) is the source of illumination preferred with a wavelength in the infrared; 2) and 3) are lenses which collimate the beam' 4) is a beam splitter which separates the paths of the input and output beams, 5) is a mirror, 6) reflects infrared light and transmits visible light, 7) and 8) are lenses that form a telescope 9) is the eye, 10) is an adjustable aperture, both in size and centration on the return path, 11) is a lens, 12) is an adjustable pinhole, 13) is a detector, 14) allows adjustments in the fixation module, 15) is a lens and 16) is a fixation target, the input beam is solid and of a smaller diameter, the ongoing beam is solid and less dark and a larger diameter than the ingoing beam and the beam from the fixation target is dashed.

The preferred implementation is shown in FIG. 8. The preferred wavelength for the instrument is 830 nm as the analysis described herein has shown that resolution reduces much less than would have been expected in the presence of diffraction alone as one moves to this wavelength which has much higher illuminations that correspond to eye safe levels than for visible light, it does not produce a pupil constriction and it is more comfortable for the individual whose eye is being examined.

An implementation of the methods and apparatus described here could be to retrofit our proposed improvements to one of several known designs for retinal or fundus imaging systems. A well-known method uses unequal entrance and exit pupils in such a way that only one of those pupils contributes to the image quality on the retina. This is also our preference. Although any of the designs resulting in single pass image quality are possible implementations, here we will describe a novel design where it is the size and position of the pupil of the eye that the light exits through that determines the image quality on the retina. This in turn is our preferred implementation in a scanning laser ophthalmoscope. In contrast, in the traditional configuration for a scanning laser ophthalmoscope the entrance pupil for ingoing light determines the resolution of the imaging and the pupil seen by the exiting light is very large. In each of the configurations described above which are equivalent to a single pass, the final image viewed with the instrument will then be blurred by the single pass point spread function and will differ in feature size by the magnification of the retina (or fundus) imaging instrument.

In our design, the light path onto the retina is through a relatively small ocular entrance pupil (~2 mm) which gives a large, diffracted point spread function on the retina. The light returning to the instrument from the retina then exits through an optimal (optimum) pupil size projected onto the entrance pupil of the eye, defined to maximize the image quality metric of choice. This will be larger enough than a 2 mm pupil at the eye (at least 2.7 mm, dependent on age) to have a smaller optical blur and to give the primary contribution to the resulting quality of the image of the retina. This still has the advantage of collecting returning light through the larger of the two pupils. Its advantage is that it allows optimum imaging in "single pass" in older individuals in whom one would need to use dilation drops to produce the very large returning pupil used in the traditional configuration of an optimum entrance pupil and a much larger exit pupil.

Given this preferred design, the ideal pupil size and centration being found are those of the entrance pupil of the eye. Once these have been found they define the pupil for the light exiting the eye into the retinal imaging instrument. The beam of light illuminating the retina is much smaller.

We then follow the detailed methodology given in the claims to determine the size of the optimum (optimal) pupil for light exiting the eye for each individual. In order to allow the implementation of this optimum pupil size in the instrument, the aperture in the instrument accepting the light returning from the eye must be adjustable such that its diameter, projected into the entrance pupil of the eye is at least 2.7 mm and is adjustable up to 5 mm, the anticipated largest returning pupil for an optimum pupil size for at least one image quality metric for a young individual. It should be adjustable to within 0.2 mm. The simplest implementation of the optimum pupil size which we have shown varies with each individual, is the use of an a continually adjustable iris conjugate with the entrance pupil for the returning light and calibrated for the pupil sizes to be produced in the eye's entrance pupil, outlined above.

To determine the optimal (optimum) centration of the pupil collecting the exiting light, we again follow the methodology in the claims. For the subsequent adjustment of pupil centration to its optimal, in the horizontal and vertical the iris containing the adjustable pupil aperture should initially be able to be centered at the centre of the eye's natural pupil and have a travel within the eye's pupil of ±0.4 mm in each of the horizontal and vertical directions, movable in increments of 0.1 mm. The adjustment of the centration will involve a translation of the iris aperture that defines the optimal pupil size to an optimal position of centration.

For the subsequent adjustment of the aperture of the pinhole in front of the detector, we again follow the methods given in the claims. Most detectors have a reasonable surface area. In a scanning laser ophthalmoscope, taking account of the acceptance angle of the detector, light in the final return path is usually focused onto the detector surface. In this design, there is a variable pinhole introduced just in front of the detector and the returning light is focused onto the pinhole. We expect that ideal pinhole size will depend on the aberrations of the eye which in turn will depend on the eccentricity of the imaging beam from the optical axis. For scanning laser ophthalmoscopes designed to image a smaller field of view a pinhole size of as low as 1.5 times the diameter of the diffraction limited spot at the detector is expected to give a sharper image and good light throughput. For a larger field of view, as is our preferred implementation, the size of the detector pinhole should be larger at about 2-3 times the size of the diffraction limited spot. Our preferred implementation is between a 50 deg to 100 deg field of view with a zoom feature that would allow higher resolution in selected smaller fields of view. Thus a variable detector pinhole size would be ideal, at the low end ranging from 1 to 3 times the size of a diffraction limited spot at the detector and ranging as high as twice the radius of the 70% encircled energy of the most aberrated eye with the ability to adjust it by increments of 0.5 times.

The method may be implemented on any retinal or fundus imaging instrument in the design of which the pupil controlling the ingoing light and the pupil controlling the outgoing light are chosen to be of unequal sizes and of such sizes that one of the two pupils primarily determines the quality of the image formed of the fundus or retina and where the size and or centration of said pupil at the eye is chosen close to its optimum value to give improved image quality when imaging a particular individual or group of individuals.

The method may be implemented on any retinal or fundus imaging instrument in a preferred implementation which uses a smaller pupil associated with the ingoing light and a larger (closer to optimum sized) pupil on the outgoing path where the size of said pupil in the entrance pupil of the eye can change to achieve its optimum size to give improved image quality when imaging individuals from different groups needing different sized optimum pupils.

The method may be implemented in a preferred implementation which uses a smaller pupil associated with the ingoing light and a larger (close to optimum sized) pupil on the outgoing path where the size of said pupil in the entrance pupil of the eye is chosen close to its optimum size to give improved image quality when imaging a particular group of individuals.

The method may be implemented in a preferred implementation which uses a smaller pupil associated with the ingoing light and a larger (close to optimum) pupil on the outgoing path where the centre of said pupil in the entrance pupil of the eye can be changed to achieve its optimum position to give improved image quality when imaging individuals needing different centration of their optimum pupils.

The size of said pupil in the entrance pupil of the eye is chosen close to its optimum size to give improved image quality and the size of the pinhole in front of the detector is also chosen to improve image quality, based on the optimum pupil size and the groups of individuals to be imaged.

The method may be implemented in a preferred implementation which uses a smaller pupil associated with the ingoing light and a larger (close to optimum sized) pupil on the outgoing path where the size of said pupil in the entrance pupil of the eye is adjustable to its optimum size to give improved image quality for individuals and the size of the pinhole in front of the detector is also chosen to improve image quality when imaging a particular group of individuals.

REFERENCES

Artal, P, Ferro, M, Miranda, I, Navarro, R (1993) Effect of aging in retinal image quality. Journal of the Optical Society of America. A, 10(7):1656-62. DOI: 10.1364/JOSAA.10.001656

J J Hunter, C J Cookson, M L Kisilak, J M Bueno, and M C W Campbell (2007). Characterizing image quality in a scanning laser ophthalmoscope with differing pinholes and induced scattered light Journal of the Optical Society of America A Vol. 24, Issue 5, 1284-1295.

Elsner, A E, Miura, M, Burns, S A. Beausencourt, E, Kunze, C, Kelley, L M, et al. (2000) Multiply scattered light tomography and confocal imaging: detecting neovascularization in age-related macular degeneration. Optics Express Vol. 7, Issue 2, pp. 95-106.

Schram, S, Schikowski, P, Lerm, E, Kaeding, A, Haueisen, J, Baumgarten, D (2016) Shack-Hartmann-based objective straylight assessment of the human eye in an increased scattering angle range. J. of Biomedical Optics, 21(7), 076003 https://doi.org/10.1117/1.JBO.21.7.076003.

Cochener, B, Patel, S N, Galliot, F (2015). Correlational Analysis of Objective and Subjective Measures of Cataract Quantification. Journal of Refractive Surgery Vol. 32, No. 2. https://doi.org/10.3928/1081597X-20151222-01.

Kuroda, T, Fujikado, T, Maeda, N, Oshika, T, Hirohara, Y, Mihashi, T (2002) Wavefront analysis in eyes with nuclear or cortical cataract. American Journal of Ophthalmology Volume 134, Issue 1, July, Pages 1-9.

Shahidi, M; Blair, N P; Mori, M; Zelkha, R (2004). Optical Section Retinal Imaging and Wavefront Sensing in Diabetes. Optometry and Vision Science: October 2004—Volume 81—Issue 10—p 778-784.

Adnan X, Suheimat M, Mathur A, et al. (2015) Straylight, Lens Yellowing and Aberrations of Eyes in Type 1 Diabetes. Biomed Opt Express 6:1282-92.

Özyol, P; Özyol, E (2018). Assessment of Corneal Backward Light Scattering in Diabetic Patients. Eye & Contact Lens: Science & Clinical Practice, September 2018—Volume 44—Issue—p S92-S96.

Valeshabad, A K, Wanek, J, Grant, P, Lim, J I, Chau, F Y, Zelkha, R, Camardo, N, and Shahidi, M (2015) Wavefront error correction with adaptive optics in diabetic retinopathy. Optom Vis Sci. 2014 October; 91(10): 1238-1243. doi: 10.1097/OPX.0000000000000252.

Liu, J, Wang, X. Wang, J, Guo, H (2019) Optical Quality and Intraocular Scattering in the Diabetic Eye without Diabetic Retinopathy. Optom Vis Sci. 2019 April; 96(4): 248-255. Published online 2019 Mar. 21. doi: 10.1097/OPX.0000000000001360

Van den Berg (2017) The (lack of) relation between straylight and visual acuity. Two domains of the point-spread-function. Ophthalmic and Physiological Optics, Vol 37, Issue 3 May 2017 333-34

Sahin, O; Pennos, A; Ginis, H; Hervella, L; Villegas, E A; Canizares, B; Maria Marin, J; Pallikaris, I; Artal, P (2016). Optical Measurement of Straylight in Eyes with Cataract. Journal of Refractive Surgery, Vol 32, Issue 12, 846-850. DOI: 10.3928/1081597X-20160920-02

Donnelly W J, Roorda, A (2003). Optimal pupil size in the human eye for axial resolution, J. Opt. Soc. Am. A 20, 2010-2015.

LaRocca, F; Dhalla, A, Kelly, M, Farsiu, S and Izatt, J (2013) Optimization of confocal scanning laser ophthalmoscope design J Biomed Opt. 18(7): 076015.

Goncharov, A V and Dainty, C (2007). Wide-field schematic eye models with gradient-index lens. Journal of the Optical Society of America A Vol 24, issue 8, 2157-2174.

Navarro, R (2014) Adaptive model of the aging emmetropic eye and its changes with accommodation. Journal of Vision November Vol. 14, 21. doi:https://doi.org/10.1167/14.13.21

Wilson, M. A., Campbell, M. C. W. and Simonet, P. (1992) The Julius F. Neumueller Award in Optics, 1989: Change of pupil centration with change of illumination and pupil size. Optometry and Vision Science 69, 129 136.

Bing, L., and Campbell, M. C. W. (1994). The change of monochromatic aberrations with lens tilt and pupil decentration in a four aspheric surface model eye. 4th Canadian Universities Conference in Optometry, Kitchener, 1994.

Navarro, R; González, L M; Hernández-Matamoros, J L. (2006) On the prediction of optical aberrations by personalized eye models. Optometry and Vision Science: Vol. 83, Issue 6, p 371-381.

Liang, J., Williams, D. R. & Miller (1997) Supernormal vision and high-resolution retinal imaging through adaptive optics, Journal of the Optical Society of America A, Vol 14, Issue 11, 2884-2892 https://doi.org/10.1364/JOSAA.14.002884.

Roorda, A., Romero-Borja, F., Donnelly, W. J., Queener, H., Hebert, T. J. & Campbell, M. C. W. (2002) Adaptive optics scanning laser ophthalmoscopy. Opt Express, 10(9):405-12 doi: 10.1364/oe.10.000405.

Mouroulis, P (2022) Optical Design Accessed via the Wiley Online Library 2022.

Marcos, S, Burns, S. A., Moreno-Barriusop, E., Navarro, R. A new approach to the study of ocular chromatic aberrations. Vision Research 39 4309-4323.

Fernandez, E. J., Artal, P. (2008) RMS wavefront aberrations are unchanged in microns from the red to the infrared wavelengths. Optics Express Vol 16, Issue 26, 21199.

Bueno, J. M. Perez, G. M. (2010) Combined effect of wavelength and polarization in double-pass retinal images in the human eye. Vision Research Vol 50, 2439-2444.

Simonet, P. and Campbell, M. C. W. (1990) The optical transverse chromatic aberration on the fovea of the human eye. Vision Research, Vol 30, Issue 2, 187-206. https://doi.org/10.1016/0042-6989(90)90035-J.

Thibos, L. N., Bradley, A., Still, D. L., Zhang, X., Howarth, P. A. (1990) Theory and measurement of ocular chromatic aberration. Vision Research, Vol 30, Issue 1, 33-49. https://doi.org/10.1016/0042-6989(90)90126-6.

Therefore what is claimed is:

1. A method for improving optical images of the retina or fundus, comprising the steps of:
    a) choosing a wavelength of light for imaging
    b) focusing the instrument on the feature of interest on the retina/fundus
    c) deciding what metric of image quality resulting from imaging through the optics of the eye is most important to the purpose of imaging the retina or a portion of the retina (eg lateral versus depth resolution versus overall image quality metrics versus the contrast of features of a particular size);
    d) choosing an additional parameter or parameter(s) to be adjusted as one or more of pupil size, pupil centration, and/or detector pinhole size;
    e) determining which group(s) the individual falls into where the property defining said group(s) or subgroup (s) is known or suspected to change the optical quality of the eye and in turn the best values of the adjustable parameter(s) on the instrument and where groups may include but are not limited to one or more of age, the presence of diabetes, and the presence of cataract or pre-cataract;
    f) with knowledge of the overall optical quality as described by the magnitude of the wavefront aberrations across the pupil of an individual's eye or of the eyes of a group into which the individual falls, consult the previously calculated value of an adjustable parameter of the fundus imaging system that will give the best value of the metric chosen in b) or estimate from the RMS of the wavefront aberration of individual the value of the adjustable parameter that will give the best value of that metric or calculate from the wavefront aberrations of the individual the value of the adjustable parameter that will give the best value of that metric;
    g) adjust the adjustable parameter of the instrument in c)
    h) repeat d) e) and f) for other adjustable parameters i) perform a visual check of perceived image quality to determine any final adjustments.

2. The method according to claim 1, wherein the parameter to be adjusted (chosen) is the wavelength of light for a mode of imaging that uses light reflected from the retina and is not considering either imaging structures that absorb infrared light, or a mode like fluorescence that requires a visible wavelength, the wavelength of choice is in the infrared as the small loss in resolution (or other image quality metric) is counterbalanced by the ability to image with increased comfort, without dilating drops and with increased patient comfort.

3. The method according to claim 1, wherein the group that the individual falls into includes only one of an age group, or a group with a condition known to affect the optical quality of the eye as a function of a measure of the severity of the condition, including but not limited to diabetes where severity may be given by diabetes duration, a measure of HbA1c or a measure of the lens thickness; and cataract whose severity is defined via a measure of scattered light or a other severity scale; the value of an adjustable parameter of the fundus imaging system that will give the best value of that metric has been previously determined and the individual has no other group memberships which are known to affect the optical quality of the eye for which the adjustable parameter has been defined.

4. The method according to claim 1, wherein in step e) "consult the previously calculated value of an adjustable parameter of the fundus imaging system that will give the best value of the metric chosen" describes a calculation that consists of calculating the chosen image quality metric as a function of the adjustable parameter (for example pupil size) and identifying the value of the adjustable parameter that gives the best value of the image quality metric either for an individual or for the average of individuals that share a common descriptor (for example a small age range).

5. The method according to claim 4, wherein "calculating the chosen image quality metric as a function of the adjustable parameter" for the group which an individual falls within consists of, following the steps taught herein for each individual of a) to f) and then in step g) taking group averages as described:
 a) determining the metric of image quality of most applicability to the feature(s) of interest on the retina/fundus
 b) measuring the wavefront aberrations of the eye using any known method for a larger pupil, induced in dim light of via dilation of the pupil with a substance and then proceeding with the steps described herein to determine the optimum pupil size and corresponding best image quality metric as a function of the metric being considered where these steps consist of
 c) creating a phase plate in the entrance pupil of a model paraxial eye consisting of the measured wavefront aberrations of each individual;
 d) calculating either the point spread function (PSF) the modulation transfer function (MTF) on the retina or any other property from which the metric of interest of the image on the retina can be calculated as a function of the adjustable parameter (for example pupil size);
 e) calculating the metric of image quality of interest from the one of the PSF or the MTF or other property as a function of the adjustable parameter (for example lateral resolution);
 f) choosing the value of the adjustable parameter that gives the best value of the image quality metric for each individual within a group (for instance defined by a small age range);
 g) averaging the value of adjustable parameter across the individuals within the given group to give the optimum parameter and then calculating the average of the chosen image quality metric, (for example the radius of 50% encircled energy representing lateral resolution).

Figure 7:
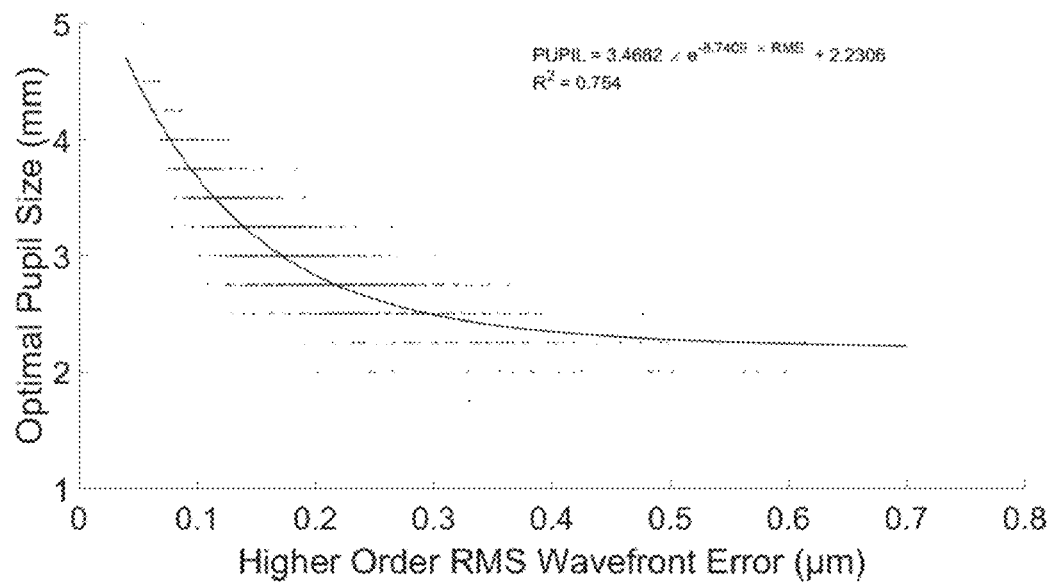
FIG. 7 gives values of the root mean squire of the higher order wavefront errors (RMS error) in microns of each individual at a maximum 5 mm pupil against that individual's optimal pupil size for best lateral resolution (based on the radius of the circle which encompasses 50% of the light within the point spread function). A fit of the optimal pupil size in millimeters to an exponential function of the RMS error in microns across individuals gives a highly significant fit with an R squared value of 0.754. Thus, the root mean square of the wavefront error across the pupil for an individual can be used as a single predictor of the optimal pupil size for the given metric of image quality, in this case best lateral resolution.

6. The method of claim 1, wherein the group that the individual falls into is a group with a condition known or suspected to affect the optical quality of the eye for which there is a need in claim 1e) to estimate the value of the adjustable parameter that will give the best value of that metric; then the estimate of the best value of the metric should follow the steps taught herein of measuring the higher order wavefront aberrations of the eye using any known method for a larger pupil, induced in dim light or via dilation of the pupil with a substance; calculating the root mean square (RMS) value of the higher order aberrations and then reading from a plot similar to that in FIG. 7 to give the optimum pupil size and corresponding best value of the chosen image quality metric as a function of the RMS higher order wavefront error.

7. The method of claim 1, wherein the group that the individual falls into is a group with a condition known or suspected to affect the optical quality of the eye which differs from previous conditions considered for which there is a need in claim 1e) to estimate or calculate the value of the adjustable parameter that will give the best value of that metric and following the methods in claim 5 to get an estimate does not give an improved image; then the calculation of the best value of the metric should follow the steps taught herein of
 a) measuring the wavefront aberrations of the eye using any known method for a larger pupil, induced in dim light of via dilation of the pupil with a substance and then proceeding with the steps described herein to determine the optimum pupil size and corresponding best image quality metric as a function of the metric being considered where these steps consist of
 b) determining the metric of image quality of most applicability to the feature(s) of interest on the retina/fundus
 c) creating a phase plate in the entrance pupil of a model paraxial eye consisting of the measured wavefront aberrations
 d) calculating either the point spread function (PSF) the modulation transfer function (MTF) or any other property of the image on the retina as a function of the adjustable parameter;
 e) calculating the metric of image quality of interest from the either the PSF or the MTF as a function of the adjustable parameter
 f) choosing the value of the adjustable parameter that gives the best value of the image quality metric;
 g) proceeding with d) to g) of claim 1.

8. The method of claim 1, wherein the image quality metric chosen can correspond to a property of the PSF or MTF at a single point on the retina, close to a feature of interest in the image, or can be for the point at which the optical axis intersects the retina or can be the weighting of said chosen metric across the field of view of the region of the retina of interest.

9. The method of claim 7, wherein the individual falls into two or more groups with a condition known or suspected to affect the optical quality of the eye for which there is a need in claim 1d) to estimate or calculate the value of the adjustable parameter that will give the best value of that metric and following the methods in claim 3 does not give an improved image.

10. The method of claim 5, wherein step b) and c) are replaced by the single step of
   b) using a known or new eye model whose optical quality is designed to reproduce the properties of a specific group (for example older persons) or to have optical properties that are a function of a specific variable (for example age).

11. The method of claim 1, wherein the metrics of image quality considered include a known metric of lateral resolution, including but not limited to the radius of the point spread function that encircles 50% of the light intensity in the PSF, a known metric of depth resolution, a known metric of overall image quality, including but not limited to the Hopkins ratio or the volume under the MTF and the contrast reduction given in the image for a feature of interest of a known size.

12. The methods of claim 1, wherein the adjustable parameter(s) of the instrument may include an entrance pupil for the instrument whose size can be adjusted from a smaller value of less than 3 mm diameter at the eye to a larger value of greater than 4 mm diameter at the eye in increments of 0.25 mm or smaller; an entrance pupil whose centre position may be adjusted vertically and horizontally with respect to the centre of the natural or artificially dilated pupil of the eye or the Purkinje image(s) of the cornea and or the crystalline lens in increments of 0.2 mm or less; a pinhole in front of the detector whose size can be adjusted from 1.5× the spot size of the diffraction limited spot at the detector for the optimum pupil chosen up to 5× the spot size; for the choice of optimum pupil size and the choice of wavelength of the incident light.

13. The methods of claim 1, wherein the wavelength of the incident light provided by the instrument has been chosen in advance of the instrument's construction based on the imaging of a given group or ocular condition for which a particular wavelength is advantageous to image quality; for instance infrared light for imaging the older eye as taught herein.

14. The methods of claim 1, wherein the parameters being adjusted are adjusted in a given order; with the wavelength being chosen first, followed by the pupil size followed by the pupil centration, followed by the detector pinhole size.

15. The methods of claim 1, wherein in step d) the parameter to be adjusted is pupil centration.

16. The methods of claim 15, wherein in order to determine the optimum centration of the pupil with respect to the pupil for which the wavefront aberrations were measured, use an aperture the size of the optimum pupil surrounded by a filter opaque to visible light but which allows the illumination of the ocular structures surrounding the pupil in infrared light; then use as a reference to locate the movable pupil with respect to the original pupil centre which is not limited to one of a) a landmark on the retina, b) a reflection associated with an ocular component, for example the first Purkinje image which is a reflection from the cornea or c) the subjective achromatic axis of the eye; then follow the steps of moving the optimum pupil size across the wavefront aberration map in the horizontal direction in increments of ±0.1 mm over 0.6 mm in first the horizontal, finding the optimal position and then moving in the vertical direction in increments of ±0.1 mm over 0.6 mm, where for each position the value of the chosen image quality metric is calculated and the best value is found following the same procedure as calculating the best value of the chosen image metric as a function of pupil size where if the value of the metric of interest calculated across the wavefront error for a particular pupil centration gets worse, then the opposite direction of placement of the pupil centre can be tested.

17. The methods of claim 1, wherein in step d) the parameter to be adjusted is detector pinhole size.

18. The method of claim 17 wherein the following steps are followed: 1) For the optimum pupil size for each individual, if not previously calculated, calculate the image quality metric of 50% encircled energy of the point spread function and take this value times two as an estimate of the diameter of the central area of the PSP; 2) Repeat the calculation for the 70% encircled energy to get a second, larger estimate of the diameter of the central area; 3) Take the averages and standard deviations of the values in 1) and 2) across the group of individuals for the value of a particular descriptor (eg age or diabetes duration); where the resulting values are estimates of the sizes as projected onto the retina of the minimum and maximum pinhole diameters to be explored; 4) if the wish is to emphasize depth resolution, set the diameter of the pinhole to between 2 and 3 times the diameter estimated of the central area of the PSF from 50% encircled energy; 5) If the wish is to improve the contrast of the image by excluding scattered light, at low power, hold the scanning beam stationary initially while the beam illuminates the centre of the desired imaging area on the retina and determine the intensity of the light captured before and after the pinhole is adjusted to the two sizes (corresponding to 50% and 70% encircled energy where if there is little change in intensity between the diameters given by 70% and 50% values, use the diameter from 50% encircled energy; otherwise use the 70% value; 6) and in eyes known to have larger amounts of scattered light (older and/or other conditions), if the light intensity goes up substantially between the smaller and larger pinhole diameters, use the larger value; 7) then after placing the beam back in scanning beam mode, compare the brightness and contrast of the image before and after the insertion of the pinhole and/or as the pinhole diameter is adjusted by small amounts; and 8) choose a pinhole diameter which gives a high contrast image which has a full range of intensities as sampled by the detector; then 8) If desired, steps 1) to 7) may be repeated for midperipheral and peripheral features of interest on the retina a value of the pinhole may be chosen which gives acceptable brightness and contrast for all three positions.

19. The method of claim 1, implemented on any fundus or retinal imaging instrument, including but not limited to fundus cameras, including still and video versions, scanning laser ophthalmoscopes, and any other ophthalmoscope and or optical coherence tomography instruments.

20. The method of claim 1, implemented on any retinal or fundus imaging instrument in the design of which the wavelength of illumination for the ingoing light has been chosen based on said methods to improve the process of imaging and/or the quality of the image formed of the fundus or retina.

* * * * *